US011460431B2

United States Patent
Xu et al.

(10) Patent No.: US 11,460,431 B2
(45) Date of Patent: Oct. 4, 2022

(54) UREA BIOSENSORS AND STABILIZATION OF UREA BIOSENSORS AT ROOM TEMPERATURE

(71) Applicant: Instrumentation Laboratory Company, Bedford, MA (US)

(72) Inventors: Xiaoxian Xu, Maynard, MA (US); Prasad Pamidi, Burlington, MA (US); Hyoungsik Yim, Stoneham, MA (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 85 days.

(21) Appl. No.: 16/430,028

(22) Filed: Jun. 3, 2019

(65) Prior Publication Data

US 2020/0318152 A1 Oct. 8, 2020

Related U.S. Application Data

(60) Provisional application No. 62/830,191, filed on Apr. 5, 2019.

(51) Int. Cl.

| | |
|---|---|
| *G01N 27/327* | (2006.01) |
| *C12Q 1/00* | (2006.01) |
| *G01N 27/333* | (2006.01) |
| *G01N 33/70* | (2006.01) |
| *G01N 33/96* | (2006.01) |
| *G01N 27/30* | (2006.01) |
| *C12Q 1/54* | (2006.01) |

(Continued)

(52) U.S. Cl.
CPC ........ *G01N 27/3275* (2013.01); *C12Q 1/002* (2013.01); *C12Q 1/003* (2013.01); *C12Q 1/005* (2013.01); *C12Q 1/54* (2013.01); *G01N 27/308* (2013.01); *G01N 27/3272* (2013.01); *G01N 27/3276* (2013.01); *G01N 27/3335* (2013.01); *G01N 33/5308* (2013.01); *G01N 33/70* (2013.01); *G01N 33/96* (2013.01); *G06F 17/18* (2013.01); *G16B 25/30* (2019.02); *G16H 10/40* (2018.01); *C12Q 1/58* (2013.01); *G01N 27/3274* (2013.01); *G01N 33/5438* (2013.01); *G06F 30/331* (2020.01)

(58) Field of Classification Search
CPC ............ G01N 27/327–3272; C12Q 1/001–005
See application file for complete search history.

(56) References Cited

U.S. PATENT DOCUMENTS

| | | | |
|---|---|---|---|
| 6,071,392 A | 6/2000 | Yamamoto et al. | |
| 6,767,441 B1 | 7/2004 | Cai et al. | |

(Continued)

FOREIGN PATENT DOCUMENTS

| | | |
|---|---|---|
| EP | 1753872 B1 | 1/2014 |
| JP | 2004-528579 A | 9/2004 |

(Continued)

OTHER PUBLICATIONS

EPO computer-generated English language translation of JP 2014-153243 A, downloaded Feb. 12, 2022 (Year: 2014).*

(Continued)

*Primary Examiner* — Alexander S Noguerola
(74) *Attorney, Agent, or Firm* — Burns & Levinson LLP

(57) ABSTRACT

Disclosed is a urea biosensor that is stable at ambient temperature, and methods of making thereof.

30 Claims, 5 Drawing Sheets

(51) Int. Cl.

| | | |
|---|---|---|
| *G01N 33/53* | (2006.01) | |
| *G16H 10/40* | (2018.01) | |
| *G16B 25/30* | (2019.01) | |
| *G06F 17/18* | (2006.01) | |
| *C12Q 1/58* | (2006.01) | |
| *G01N 33/543* | (2006.01) | |
| *G06F 30/331* | (2020.01) | |

(56) References Cited

U.S. PATENT DOCUMENTS

| | | |
|---|---|---|
| 6,960,466 B2 | 11/2005 | Pamidi et al. |
| 7,285,198 B2 | 10/2007 | Douglas |
| 7,632,672 B2 | 12/2009 | Pamidi et al. |
| 7,815,788 B2 | 10/2010 | Schaffar et al. |
| 8,426,192 B2 | 4/2013 | Pamidi et al. |
| 9,487,811 B2 | 11/2016 | Zhao et al. |
| 11,293,890 B2 | 4/2022 | Xu et al. |
| 2004/0163949 A1* | 8/2004 | Sorensen ............ G01N 27/301 204/280 |
| 2004/0211666 A1 | 10/2004 | Pamidi et al. |
| 2004/0256227 A1 | 12/2004 | Shin et al. |
| 2006/0275857 A1 | 12/2006 | Kjaer et al. |
| 2007/0034512 A1* | 2/2007 | Yamaoka ............... C12Q 1/004 204/403.01 |
| 2007/0131548 A1* | 6/2007 | Winarta ................. C12Q 1/005 204/403.02 |
| 2008/0173064 A1 | 7/2008 | Schaffar et al. |
| 2013/0186755 A1* | 7/2013 | Chu ................... G01N 27/3272 204/403.14 |
| 2017/0254771 A1 | 9/2017 | Balasubramanian et al. |

FOREIGN PATENT DOCUMENTS

| | | |
|---|---|---|
| JP | 2005-501254 A | 1/2005 |
| JP | 2005501254 A | 1/2005 |
| JP | 2008-502921 A | 1/2008 |
| JP | 2008502921 A | 1/2008 |
| JP | 2011-508221 A | 3/2011 |
| JP | 2011508221 A | 3/2011 |
| JP | 2014-153243 A | 8/2014 |
| WO | 98/21356 A1 | 5/1998 |
| WO | 03/019171 A1 | 3/2003 |
| WO | 2005/052596 A1 | 6/2005 |
| WO | 2008/028011 A2 | 3/2008 |
| WO | 20080028011 A2 | 3/2008 |
| WO | 2009/053370 A1 | 4/2009 |
| WO | 2009/082699 A1 | 7/2009 |
| WO | 2016/096725 A1 | 6/2016 |

OTHER PUBLICATIONS

International Search Report and Written Opinion for International Application No. PCT/US2019/035156, dated Sep. 20, 2019, 12 pages.
International Search Report and Written Opinion for International Application No. PCT/US2019/035152, dated Nov. 8, 2019, 12 pages.
International Search Report and Written Opinion for International Application No. PCT/US2019/035155, dated Nov. 14, 2019, 12 pages.
Nichols et al., The effect of nitric oxide surface flux on the foreign body response to subcutaneous implants, Biomaterials, vol. 33, No. 27, May 20, 2012, pp. 6305-6312.
Conway et al., Layer-by-layer design and optimization of xerogel-based amperometric first generation biosensors for uric acid, Journal of Electroanalytical Chemistry, vol. 775, May 25, 2016, pp. 135-145.
Tjell et al., Diffusion rate of hydrogen peroxide through water-swelled polyurethane membranes, Sensing and Bio-Sensing Research, vol. 21, No. 27, Nov. 1, 2018, pp. 35-39.
Hydrourethane AdvanSource Biomaterials, Advancesource Biomaterials, Jun. 21, 2011 [retrieved on Sep. 19, 2019]. Retrieved from the Internet URL: http://www.advbiomaterials.com/pdf/HydroThane%20Factsheet.pdf.
International Search Report and Written Opinion for International Application No. PCT/US2019/035157, dated Dec. 12, 2019, 18 pages.
International Search Report and Written Opinion for International Application No. PCT/US2019/035153, dated Nov. 26, 2019, 12 pages.
Japanese Office Action dated Aug. 13, 2021, Japanese Application No. 2020-570928.
Notice of Reasons for Rejection for Japanese Patent Application No. 2020-571701, dated Sep. 2, 2021, (with English translation), 18 pages.
Notice of Reasons for Rejection for Japanese Patent Application No. 2020-571701, dated Dec. 24, 2021, (with English translation), 14 pages.
International Preliminary Report on Patentability dated Sep. 28, 2021, International Application No. PCT/US2019/035153 filed Jun. 3, 2019 (6 pages).
Notice of Reasons for Rejection for Japanese Patent Application No. 2020-570928, dated Feb. 2, 2022, (with English translation), 9 pages.
Communication pursuant to Rules 161(1) and 162 for European Patent Application No. 19739734.2, dated Nov. 12, 2021, 3 pages.
Communication pursuant to Rules 161(1) and 162 EPC for European Patent Application No. 19734964.0 dated Dec. 1, 2021, 3 pages.
Examination Requisition for Canadian Patent Application No. 3,104,896 dated Feb. 18, 2022, 5 pages.
Hydromed D Series, Advancesource Biomaterials, Apr. 16, 2010, [retrieved on Sep. 20, 2019]. Retrieved from the Internet URL:Http://www.advbiomaterials.com/products/hydrophilic/HydroMed.pdf.
International Preliminary Report on Patentability dated Sep. 28, 2021, International Application No. PCT/US2019/036156 filed Jun. 3, 2019, 7 pages.
Notice of Reasons for Rejection for Japanese Patent Application No. 2020-571761 dated Dec. 24, 2021, (with English translation), 14 pages.
Examiner Requisition for Canadian Patent Application No. 3,105,191, dated Feb. 17, 2022, (4 pages).
Decision to Grant for Japanese Patent Application No. 2020-570928, dated Aug. 17, 2022, 3 pages.
Julia M.C.S. Magalhaes, Urea potentiometric biosensor based on urease immobilized on chitosan membranes, Talanta, 1998, 47, pp. 183-191.

\* cited by examiner

UREA BIOSENSORS AND STABILIZATION OF UREA BIOSENSORS AT ROOM TEMPERATURE

CROSS REFERENCE TO RELATED APPLICATIONS

This application claims priority to and benefit of U.S. Provisional application No. 62/830,191, filed Apr. 5, 2019 and is incorporated in its entirety herein for all intents and purposes.

FIELD OF THE INVENTION

The present invention relates to urea biosensors and methods of making thereof, having enzyme stability at room temperature and prolonged shelf-life and use-life.

BACKGROUND

Enzyme biosensors are used to detect numerous analytes such as creatinine, creatine, glucose, urea and lactate, in a patient body fluid sample such as blood. As such, enzyme biosensors are particularly important in assisting point-of-care diagnosis of a patient malady.

However, one of the drawbacks of enzyme biosensors, particularly in point-of care applications, is loss of enzyme activity over its continuous use and over its shelf-life at ambient temperature, typically at less than 15 days. Thus, short shelf-life is a critical factor limiting the practical application of enzyme biosensors such as the urea biosensor.

The shelf-life of an enzyme biosensor that is particularly problematic is the urea biosensor. Measurement of urea is important to patient care because it is helpful for determining kidney dysfunction in a patient.

A urea sensor is a biosensor comprising an enzyme modified ammonium ion selective electrode. Urea hydrolysis, a step necessary in measuring urea in a patient sample such as blood, serum or plasma, is catalyzed by urease in a urea sensor as follows:

The product generated following urea hydrolysis catalyzed by urease is ammonium ion.

The enzyme urease is immobilized on the surface of an ammonium ion-selective electrode through a crosslinking reagent, for example, glutaraldehyde, or by physical absorption, entrapment with a hydrogel, for example, to form an enzyme layer on the electrode. The product ammonium ($NH_4$) is then potentiometrically detected by the ammonium sensor, one of the types of sensors typically in an array of sensors positioned on a substrate, or card. The sensor potential is measured against the card reference electrode (Ag/Ag+) and is proportional to the logarithm of urea concentration based on the Nernst equation.

After forming an immobilized enzyme layer on the electrode, a permeable outer polymeric membrane is applied on top of the enzyme layer of the electrode to protect the enzyme, urease in this case, from denaturation when in contact with a patient body fluid sample, and to limit the flux of the substrate urea entering the enzyme layer from the patient body fluid sample.

For commercialization, mass production and the practical application of the urea sensor described above to accurately measure urea in a biological sample, a major challenge has to be overcome. The challenge is achieving long term stability of the enzyme urease over storage (shelf-life) at least 5 months to a year or more at ambient temperatures in the range of 15-25° C., preferably 18-24° C., more preferably 20-24° C., and 24° C.

From a design principle, the urea sensor sensitivity (slope) towards measuring urea is directly related to the remaining activity of the immobilized enzyme mixture on the electrode of the biosensor. It is well known that bioactive components, such as enzymes, are very delicate and are not stable at ambient temperature for an extended period. The fast decay of the urea biosensor sensitivity (slope loss), as well as the deterioration of accuracy at high concentration towards measuring substrate urea (linearity loss) due to protein denaturation is the basis for its instability and very limited use-life or shelf-life.

Whole blood analyzers, for example the GEM Premier® analyzer (Instrumentation Laboratory Company, Bedford, Mass.) utilize a multi-use, single consumable cartridge, for example, the cartridges described in U.S. Pat. No. 6,960,466 and US Pub. No 2004/0256227A1 assigned to Instrumentation Laboratory Company (Bedford, Mass.) and incorporated by reference herein in its entirety for all intents and purposes. The cartridge contains all critical components (sensor arrays, reference solutions, rinse solutions and calibration reagents) including at least one urea sensor, for blood measurement of blood analytes and requires ambient temperature storage for a minimum of 5 months.

Most commercially available urea sensors with similar design address short urea sensor use-life and shelf-life by refrigeration of the critical parts of the biosensor to extend its shelf-life. However, this approach adds complexity to instrument operation by the field operator at point-of-care locations of the hospital. For the GEM® PAK cartridge (Instrumentation Laboratory Company, Bedford, Mass.), for example, biosensors are an integral and critical feature of the cartridge. The urea enzyme sensor is an integral part of the cartridge, and it is impractical to store the entire cartridge in refrigeration due to the pack size and reagent stability, for example, reagent stability of the reference solution and stabilization of gases pO2 and pCO2 of calibration solutions.

Other methods that have been tried to preserve urease activity in a urea sensor include changing the enzyme immobilization method from chemical cross-linking immobilization to physical adsorption (entrapment of urease with polyurethane). The entrapment method normally does not provide as strong immobilization of urease as chemical bonding by cross-linking, and mixing the enzyme in polyurethane may also impact the urea sensor response time.

It has been reported in literature that the activity of bioactive species such as enzyme either in solution form or in dry stage at free form can be preserved with mono- or polysaccharides.

Sugars may be used as stabilizers to preserve the free form enzyme during lyophilization (freeze drying). However, the specific sugar best for stabilizing one enzyme is based on the structure of the sugar, hydrophilicity/hydrophobicity of the enzyme, and its interactions with water and stabilizer.

It is hypothesized that in the presence of water, the polyhydroxyl groups contained in the sugar can form a complex with water, and this complex is able to penetrate to the enzyme structure even under the cross-linked stage. It is believed that the complex can reduce the unfolding of the enzyme structure which leads to denaturation and thus maintains activity of the enzyme.

However, having the enzyme urease sandwiched between two polymer layers in a urea sensor presents more complex interactions between the enzyme and components in the two polymer layers (ionophore, plasticizer, lipophilic salt, organic solvents, etc.) causing instability of the enzyme during preparation of the sensors or during shelf storage at ambient temperatures. These interactions lead to less than expected performance. The aim of the invention described herein is to address instability of the urea sensor due to cross interactions of the enzyme with other chemical-components with the aim to increase stability of urease during storage of the urea sensor. The invention described herein increases and relates to storage of a stable urea sensor for a minimum of 5 months at room temperature.

SUMMARY OF THE INVENTION

The present invention relates to stable urea biosensors at room temperature, methods of making, and cartridges housing the stable urea biosensor. The terms sensor and biosensor are used interchangeably throughout.

In one aspect, the invention is directed to a method for making the urea biosensor, the biosensor having stability for at least 5 months shelf-life at ambient temperature and an additional three weeks use-life. The method comprises providing an electrode, the polyvinyl chloride (PVC) based ammonium ion-selective membrane is fabricated as described in US Pub. No. 2004/0256227A1 (EP1753872B1), incorporated by reference herein, on a silver electrode surface which is covered with AgCl and an inner layer as an internal reference electrode, casting urease enzyme in solution, i.e., an enzyme mixture, on the outer surface of the PVC membrane to form an enzyme layer, applying a diffusion barrier on the surface of the enzyme layer, applying a polysaccharide solution to the urea sensor, and drying the sensor to form the stable urea biosensor.

The inner reference electrode of the biosensor, is selected, for example, from the metal group consisting of silver, platinum or gold and is covered with AgCl and an electrolyte inner layer. The inner electrolyte layer is formed by casting an inner solution, which is comprised of a MES buffer, sodium chloride, ammonium chloride, and hydroxyethylcellulose (HEC), on the Ag/AgCl electrode surface.

The urea biosensor is capable of measuring urea in a body fluid sample such as blood, plasma or serum.

The step for applying a polysaccharide solution to the urea biosensor in various embodiments includes applying one or more polysaccharides such as but not limited to the disaccharides sucrose, trehalose, and lactitol, the trisaccharide raffinose, and other polysaccharides. The polysaccharide may be added to the enzyme mixture before the sensor is cast with the enzyme mixture, or, in a solution after application of the outer diffusion membrane to the sensor, or as a combination of the above steps. After assembly, the urea biosensor may be immersed in a polysaccharide solution, dried, and re-immersed in the polysaccharide solution, followed by drying each time. Optionally, immersion of the urea biosensor into the polysaccharide solution may be repeated a plurality of times each time followed by drying. The concentration of the polysaccharide in solution is in the range of greater than 0% to about 25% and the duration of polysaccharide treatment is thirty minutes or longer.

Application of the diffusion barrier comprises applying a polymeric compound selected from the group consisting of polyurethane, poly(tetrafluoroethylene) ionomers (the perfluorosulfonate ionomer, NAFION®), poly-(2-hydroxymethyl methacrylate), polyvinyl chloride, cellulose acetate, and mixtures and copolymers thereof to the electrode to form the outer diffusion membrane that is in contact with the body fluid sample that is introduced into a body fluid sample flow chamber in which urea is to be measured. The enzyme layer is positioned between the outer diffusion membrane and the ammonium-selective PVC membrane.

A stable urea biosensor according to the method of the invention maintains a stable urea measurement performance after at least 5 months storage at ambient temperature and 21 days of use.

In another aspect, the invention is directed to a urea biosensor comprising an ammonium-selective electrode, the enzyme urease immobilized on the ammonium-selective polymer membrane as an enzyme layer, a diffusion barrier on the surface of the enzyme layer, and a polysaccharide. The electrodes, ammonium-selective polymer membrane, enzymes, cross-linkers, polysaccharides, diffusion barriers, and stability of the urea biosensor are described above.

In yet another aspect, the invention is directed to a cartridge housing at least one urea sensor in a sensor array, the at least one urea sensor comprising an ammonium-selective membrane, an enzyme layer comprising, urease, a diffusion barrier on the surface of the enzyme layer adjacent a body fluid sample flow chamber, and a polysaccharide. The urea sensor comprising electrodes, ammonium-selective polymer membrane, enzymes, cross-linkers, polysaccharides, diffusion barriers, and stability of the urea biosensor is described above. In one embodiment according to the invention, in addition to a card having a sensor array in which the enzyme biosensor according to the invention is included, the cartridge houses at least one urea sensor described above in the sensor array, and additionally includes reference solutions, fluidic channels, calibration reagents, rinse solutions and electronic components for operatively interfacing with a clinical analyzer, and other critical components.

DETAILED DESCRIPTION

The inventions described below are directed to a device and related method for enhancing enzyme stability and extending the shelf-life and use-life of urea biosensors useful in clinical analyzers for in vitro diagnostics, point-of-care applications in particular.

According to the invention, polysaccharides, for example, disaccharides, such as sucrose, are optimal compositions for preserving the stability and activity and extending the shelf-life and use-life of urea biosensors systems. Other polysaccharides such as trehalose (α-D-Glucopyranosyl-α-D-glucopyranoside), raffinose (O-α-D-Galactopyranosyl-(1→6)-α-D-glucopyranosyl β-D-fructofuranoside), and lactitol (4-O-β-D-Galactopyranosyl-D-glucitol) (all polysaccharides obtained from Sigma) also improve stability and activity of urease in urea biosensors extending its shelf-life and use-life.

For simplicity, 10% sucrose was used as an example polysaccharide for the studies presented below. Significant improvement in maintaining urease activity at ambient temperature was observed with sucrose stabilization. A stable shelf-life of at least 5 months was achieved when the urea sensor was stored at room temperature following sucrose-treatment enzyme stabilization.

As described below, it was determined by the inventors that a disaccharide, for example, sucrose, is one of the optimal compositions for preservation and stability of the activity of a urea biosensor. Other poly-saccharides such as trehalose, raffinose, and lactitol also have similar effect on urea sensors improving stability.

Figure 1:
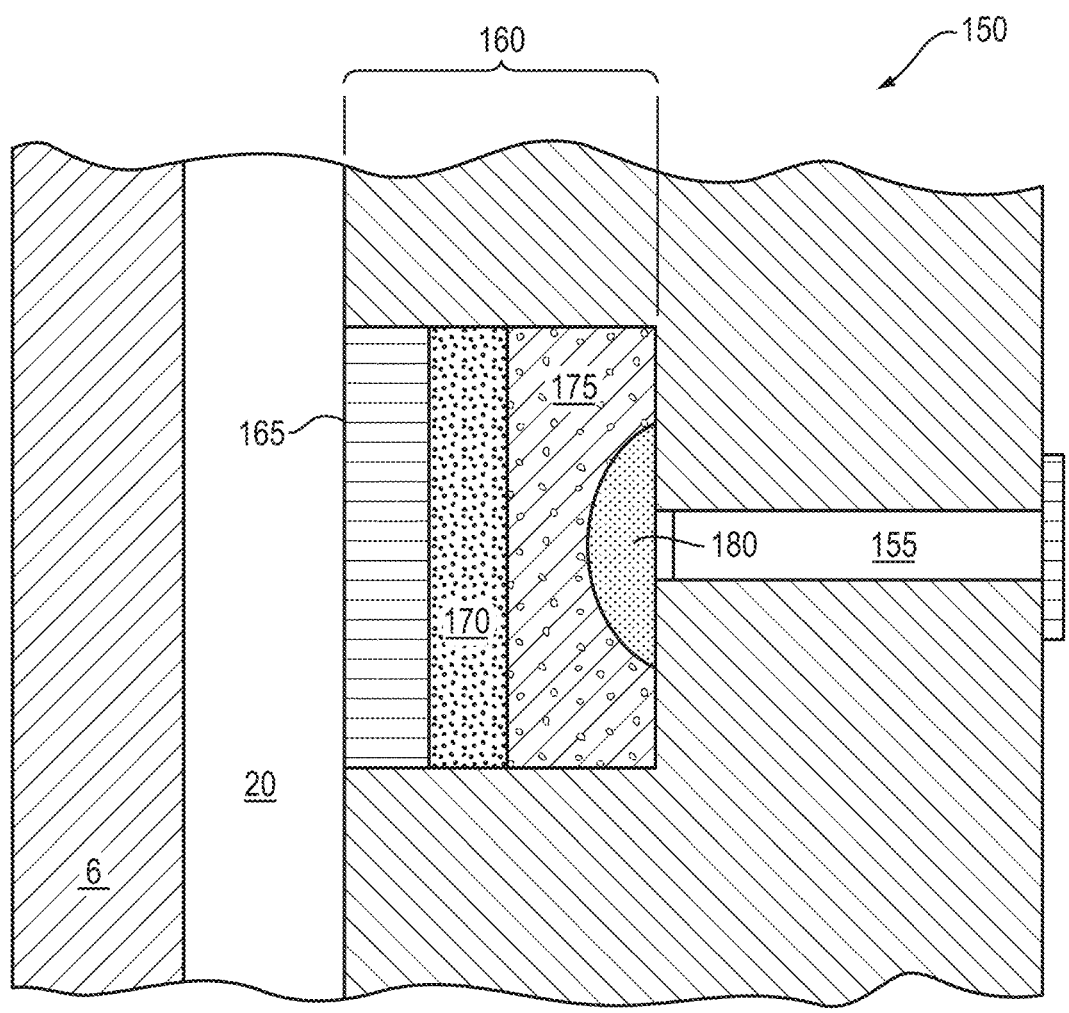
FIG. 1 is a diagrammatic illustration of a cross-section of one embodiment of a urea biosensor according to the invention.

A typical urea biosensor 150 shown in FIG. 1, comprises a metal element 155 embedded in an electrode card 6 and a composite membrane 160 which is located between the metal element 155 and an analytical sample that flows through a channel 20 in the electrode card 6. The composite membrane 160 includes an outer diffusional membrane 165 adjacent to the patient sample channel 20, an enzymatic layer 170, an ammonium-selective polymeric membrane 175, and an inner solution layer 180 adjacent the metal element 155.

The outer diffusion layer 165 controls the diffusion of the analyte into the enzyme layer 170 and protects the other components of the urea biosensor 150 from direct contact with the analytical sample in the channel 20. The enzyme layer 170 may include at least one enzyme, or a mixture of several enzymes, proteins and stabilizers that react with a particular analyte, i.e., urea in the patient sample. If the analyte diffuses through the outer diffusional membrane 165 into the enzyme layer, it can react with the enzyme in the enzyme layer 170 to produce a chemical byproduct, in the case of urea, ammonium ions. An electrical potential is generated across the composite membrane 160 that depends on the concentration of the chemical byproduct that is proportional to the concentration of urea in the analytical sample. PVC may be a constituent of the ammonium selective polymeric membrane 175.

In one embodiment of the invention, the steps for making a stable disaccharide-treated urea sensor according to the invention include:

(i) fabricating a polyvinyl chloride (PVC) based ammonium ion-selective sensor on a silver surface 155 which is covered with AgCl and inner solution layer 180 to form an internal reference electrode, the PVC ammonium ion-selective membrane 175 composition is described in US Publication No. 2004/0256227, incorporated by reference herein for all intents and purposes; followed by (ii) immobilizing the enzyme, urease, to form an enzyme layer 170 on the outer surface of the PVC membrane 175 by applying, for example, a cross-linking agent, e.g., the cross-linker, if applied, selected from the group consisting of glutaraldehyde, diisocyanatobutane, diisocyanoto, 1, 2, 7, 8-diepoxyoctane, 1, 2, 9, 10-diepoxydecane, and combinations thereof; alternatively, immobilization of one or more enzymes on the outer surface of the PVC membrane 175 can occur by physical absorption, entrapment with a hydrogel, for example; followed by (iii) applying a hydrophilic polyurethane layer to form the outer diffusion membrane 165, or one or more of the following polymers such as poly(tetrafluoroethylene) ionomers (the perfluorosulfonate ionomer, NAFION®), poly-(2-hydroxymethyl methacrylate), polyvinyl chloride, cellulose acetate, or mixtures and copolymers thereof to the enzyme layer 170 for enzyme protection and diffusion control; followed by, (iv) exposing the urea sensor 150 to a polysaccharide solution such as a sucrose solution or alternatively a solution of trehalose, raffinose, or lactitol in concentrations (w/v) ranging from >0% to 2%, 2% to 25%, 2% to 20%, 5% to 15%, 10% to 15%, preferably, 10% solution for at least 30 minutes to 24 hours, at leak 30 minutes to 240 minutes, at least 30 minutes to 120 minutes, at least 30 minutes to 60 minutes, preferably at least 30 minutes; followed by (v) air drying the polysaccharide-treated urea sensor 150; and (vi) storing, for example, 5 months or longer, the urea sensor 150 in ambient conditions until use.

In an alternative embodiment of making a stable urea biosensor 150, the steps include;

(i) fabricating a polyvinyl chloride (PVC) based ammonium ion-selective sensor on a silver surface 155 which is covered with AgCl and an inner solution layer 180 to form an internal reference electrode, the PVC ammonium ion-selective membrane 175 composition is as described above;

(ii) preparing a urease enzyme in a polysaccharide solution such as a sucrose solution or alternatively a solution of trehalose, raffinose, or lactitol in concentrations (w/v) ranging from >0% to 2%, 2% to 25%, 2% to 20%, 5% to 15%, 10% to 15%, preferably, 10% solution (iii) applying the urease enzyme-polysaccharide solution described in step (ii) and immobilizing the enzyme, urease, in the polysaccharide solution on the outer surface of the PVC membrane 175 by applying, for example, a cross-linking agent, e.g., the cross-linker, if applied, selected from the group consisting of glutaraldehyde, diisocyanatobutane, diisocyanoto, 1, 2, 7, 8-diepoxyoctane, 1, 2, 9, 10-diepoxydecane, and combinations thereof to form an enzyme layer 170; followed by, (iv) applying a hydrophilic polyurethane layer 165 or one or more of the following polymers such as poly(tetrafluoroethylene) ionomers (the perfluorosulfonate ionomer, NAFION®), poly-(2-hydroxymethyl methacrylate), polyvinyl chloride, cellulose acetate, or mixtures and copolymers thereof to the enzyme layer 170 for enzyme protection and diffusion control; followed by (v) storing, for example, 5 months or longer, the urea sensor 150 in ambient condition until use.

In yet another embodiment of making a stable urea biosensor 150, the steps include:

(i) fabricating a polyvinyl chloride (PVC) based ammonium ion-selective sensor on a silver surface 155 which is covered with AgCl and an inner solution layer 180 to form an internal reference electrode, the PVC ammonium ion-selective membrane 175 composition is as described above;

(ii) preparing a urease enzyme solution in a polysaccharide solution such as a sucrose solution in water or alternatively a solution of trehalose, raffinose, or lactitol in concentrations (w/v) ranging from >0% 2% to 25%, 2% to 20%, 5% to 15%, 10% to 15%, preferably, 10% solution;

(iii) applying the urease enzyme-polysaccharide solution described in Step (ii) and immobilizing the enzyme, urease, in the polysaccharide solution on the outer surface of the PVC membrane 175 by applying, for example, a cross-linking agent, e.g., the cross-linker, if applied, selected from the group consisting of glutaraldehyde, diisocyanatobutane, diisocyanoto, 1, 2, 7, 8-diepoxyoctane, 1, 2, 9, 10-diepoxydecane, and combinations thereof to form an enzyme layer 170; followed by (iv) applying a hydrophilic polyurethane layer 165 or one or more of the following polymers such as poly(tetrafluoroethylene) ionomers (the perfluorosulfonate ionomer, NAFION®), poly-(2-hydroxymethyl methacrylate), polyvinyl chloride, cellulose acetate, or mixtures and copolymers thereof to the enzyme layer 170 for enzyme protection and diffusion control; followed by (v) exposing the urea sensor 150 to a polysaccharide solution such as a sucrose solution or alternatively a solution of trehalose, raffinose, or lactitol in concentrations (w!v) ranging from >0% to 2%, 2% to 25%, 2% to 20%, 5% to 15%, 10% to 15%, preferably,10% solution for at least 30 minutes to 24 hours, at least 30 minutes to 240 minutes, at least 30 minutes to 120 minutes, at least 30 minutes to 60 minutes, preferably at least 30 minutes; followed by air drying the polysaccharide-treated urea sensor 150; optionally repeating the step exposing the sensor to a polysaccharide solution once, twice, 3-4, 5-8, and 9-10 times, followed by storing, for example, five months or longer, the urea sensor 150 in ambient condition until use.

EXEMPLIFICATION OF THE INVENTION

Example 1

Example 1 described below provides one embodiment of the method for making the urea sensor with sucrose stabilization.

1. According to one method of the invention, a solution for an ammonium selective polymer membrane is prepared in THF and contains, for example, 25-35% PVC, 60-70% DOS, 1-5% nonactin, and 0-1% KTpClPB by weight.

Nonactin is an ionophore with specific selectivity towards ammonium. Other reagents, for example, monactin, dinactin, trinactin, tetranactin, narasin, benzocrown ethers, cyclic depsipeptides, and mixtures of the preceding can also be used for this purpose.

DOS (bis(2-ethylhexyl) sebacate) is a plasticizer. o-nitrophenyl octyl ether (NPOE) is another commonly used plasticizer.

KTpC1PB (Potassium tetrakis[4-chlorophenyl]borate) is a lipophilic salt. Potassium tetrakis[3,5-bis(trifluoromethyl) phenyl]borate (KTTFPB) can also be used for this purpose.

Other than PVC, the polymer membrane can also include, for example, polyurethane, poly(tetrafluoroethylene), poly (methyl methacrylate), silicone rubber, and mixtures of above.

THF (tetrahydrofuran) is a solvent. Cyclohexanone can also be used for this purpose.

2. The ammonium sensor is planar and formed by casting the ammonium selective polymer membrane solution made as described above on a Ag/AgCl metal electrode and an inner electrolyte layer to form an internal reference electrode which is embedded in a solid substrate, for example, but not limited to PVC. The inner electrolyte layer is formed by casting the inner solution on the Ag/AgCl electrode surface. The inner solution contains, for example, a 65% MFS buffer, 1% sodium chloride, 1% ammonium chloride, and 33% HEC (percentages by weight) in water.

3. The enzymatic layer is formed by casting an enzyme solution on the outer surface of the ammonium-selective PVC membrane. The enzyme solution includes an enzyme urease, enzyme stabilizer glutathione, inert proteins bovine serum albumin, cross-linking agent glutaraldehyde and solvents. Glutathione is used together with one or more inert proteins, e.g., bovine serum albumin, to stabilize the urease in the enzyme layer. Cross-linking also secures the enzymatic layer to the underlying ion-selective polymeric layer. During fabrication of the enzymatic layer, the enzyme stabilizers are generally added to the solution containing the enzyme prior to the addition of the cross-linking agent to ensure the stabilizers are cross-linked together with the enzyme. A typical enzyme solution was prepared containing 50 mg/mL urease, 20 mg/mL glutathione. 10 mg/mL bovine serum albumin, and 0.12% glutaraldehyde in 0.1 M phosphate buffer at a pH of 7.2, and the solution was applied to the top of the ammonium ion-selective PVC membrane.

4. Polyurethane (KJ) is one of the polymers that has superior biocompatibility in many successful in vivo and in vitro applications in medical devices. The specific hydrophilic medical grade polyurethane families selected to be optimized for this application are Tecophlic™ and Tecoflex™ from Lubrizol (Wickliffe, Ohio). These commercially available polymeric resins are aliphatic, polyether-based polyurethane which can be dissolved in organic solvents or mixture of solvents such as dimethylacetamide (DMA), tetrahydrofuran (THE), etc. Within these polyurethane families, there are different grades of materials available with the combination of various hardness and water uptake levels for different applications. The outer diffusional membrane of the urea biosensor in contact with the patient sample in various embodiments includes one or more distinct layers of identical or different polymers and/or identical or different co-polymers. A typical outer diffusional membrane solution was prepared containing 0.12 g/ml polyurethane (Lubrizol, Wickliffe, Ohio) in THF. The outer diffusional membrane solution was applied over the enzyme layer to form the outer diffusional membrane. Other than polyurethane, one or more of the following polymers can also be candidates for the outer diffusional membrane, NAFION® (the poly(tetrafluoroethylene) ionomers), poly-(2-hydroxymethyl methacrylate), polyvinyl chloride, polycarbonate, and cellulose acetate.

5. In one embodiment of the invention, the urea sensor with composite membrane of inner layer—PVC layer—Enzyme layer—polyurethane layer is then immersed in a disaccharide solution, for example, a sucrose solution, in concentrations ranging from ranging from >0% to 2%, 2% to 25%, 2% to 20%, 5% to 15%, 10% to 15%, preferably, 10% solution for at least 30 minutes to 24 hours, at least 30 minutes to 240 minutes, at least 30 minutes to 120 minutes, at least 30 minutes to 60 minutes, preferably at least 30 minutes. The sucrose solution is buffered at biological pH of 7.4.

6. The sensor is dried at room temperature for 0.5 hours to 3 hours. Optionally, sucrose treatment is repeated multiple times followed by air drying each time. The sensor is then stored at ambient temperature until use.

Example 2

Example 2 is a study to assess the effect of sucrose treatment on stabilization of urea sensor described above at ambient temperature using a multi-factorial experimental design that was carried out with three main factors (each at two conditions) to investigate—(i) the delay time (2 or 7 days) between the sensor fabrication and exposing the fabricated sensor to the sucrose solution, (ii) the soak time (2 or 16 hours) during which the sensor is exposed to the sucrose solution, and the drying time (0.5 or 3 hours) after the sucrose exposure is completed. A subgroup of urea sensors were assembled into cartridges and urea concentration was measured in GEM® Premier clinical analyzers for use-life stability. An aqueous sample having a high concentration of urea (70 mg/dL) was tested daily on the urea sensors in the cartridges to assess the linearity of urea sensor measurement.

Figure 2A:
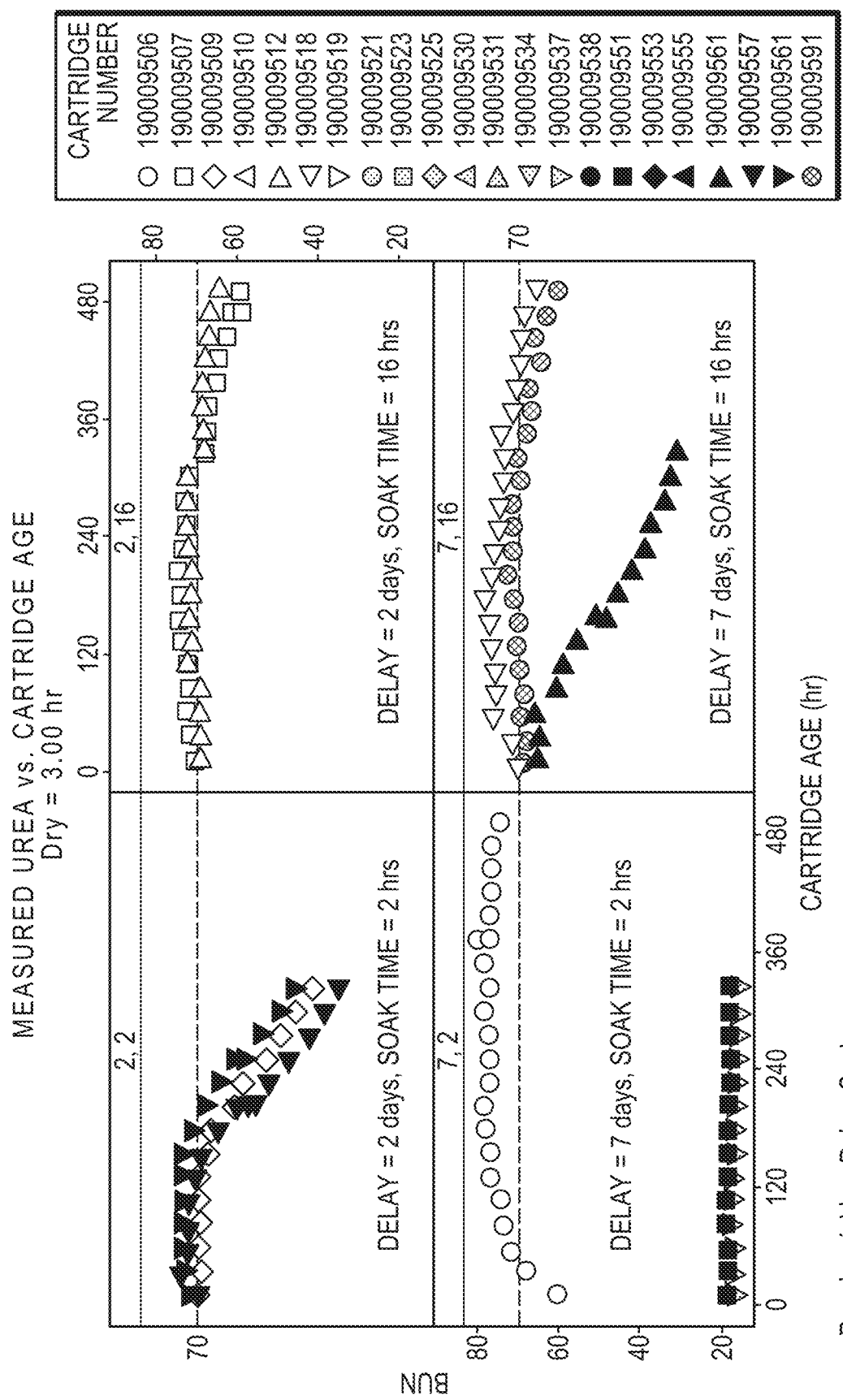
FIG. 2A is a graphic illustration of the effect of sucrose treatment on linearity of urea measurement in twenty-two urea sensors; the measurement of high urea concentration (70 mg/dL) in a sample versus cartridge age with drying time of 3 hours after sucrose treatment.
Figure 2B:
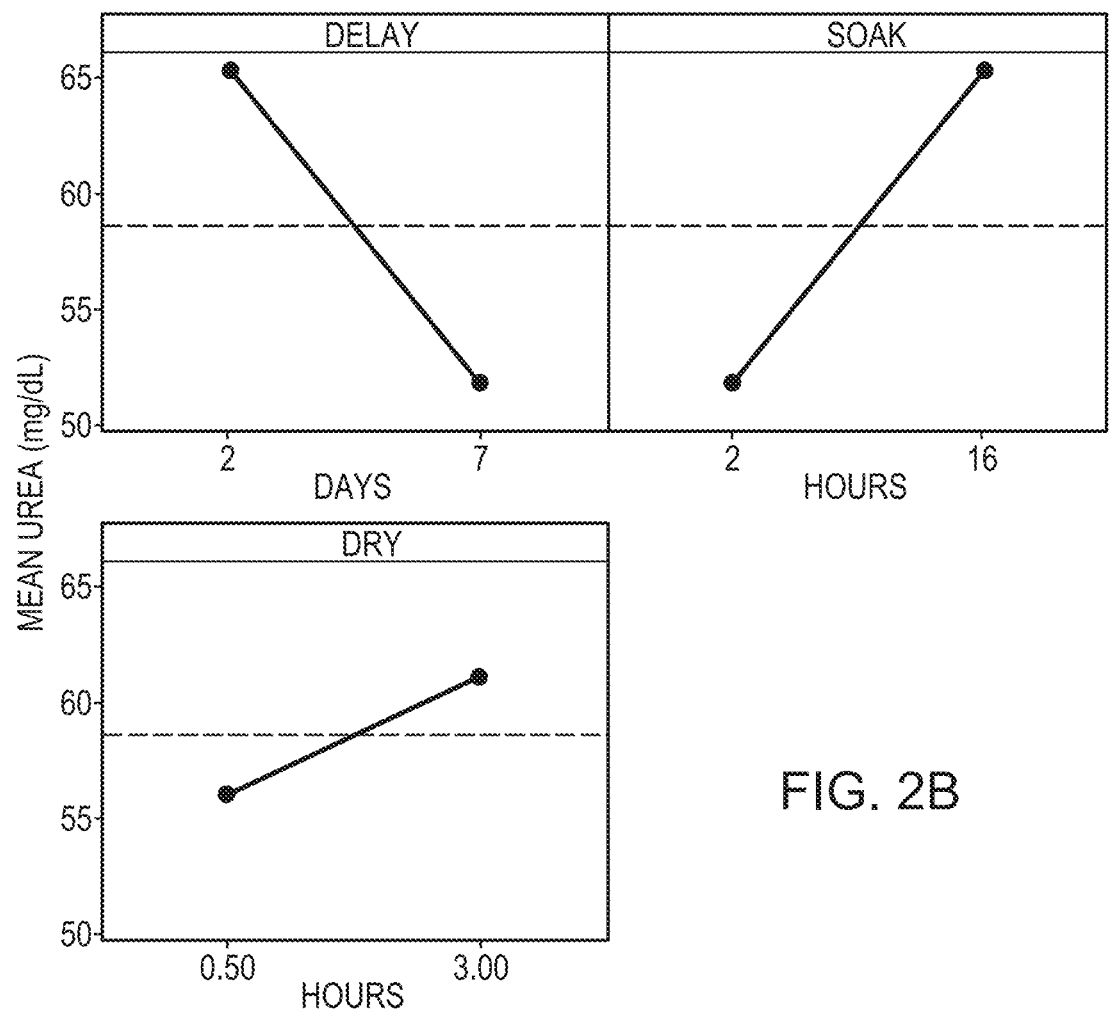
FIG. 2B is a graphic illustration of the impact of sucrose treatment on urea measurement (mg/dl) for combinations of two of three sucrose treatment factors (time delay (days) from sensor fabrication to sensor disaccharide treatment; length of disaccharide treatment soak time (hours); length of disaccharide treated sensor drying time hours) on the twenty-two urea sensors in FIG. 2A.

Referring to FIG. 2A, the use-life stability of each of the tested urea sensors at various applied experimental conditions when the drying time is fixed at 3 hours is provided. FIG. 2B illustrates the effect of the experimental conditions on urea measurement.

The results shown in FIG. 2A are readily summarized. The condition applied with shorter delay time (2 days) and longer soak time (16 hours) in 10% sucrose solution provided the most stable performance over the use-life of the sensor and most consistent sensor-to-sensor performance. The poorest stabilization performance occurred with the condition of longer delay time (7 days) combined with shorter soak time (2 hours) in 10% sucrose solution. The other two conditions provided better performance compared to the poorest performance of 7 day delay time/2 hour soak time but also exhibited inconsistency from sensor-to-sensor (7 days, 16 hours), or performance deterioration over the-use-life (2 days, 2 hours). FIG. 2B illustrates urea measurement and the favorable direction for all three sucrose treatment condition factors: shorter delay time, longer soak time and longer drying time.

These results confirmed that urease enzyme activity in a urea biosensor that is disaccharide treated is continuously undergoing decay even when urease is immobilized on the sensor. The quicker the fabricated sensor is exposed to sucrose treatment, the better urease activity is preserved. These studies also indicated that removal of all moisture, by drying, is critical for long term enzyme stability.

Example 3

Example 3 provides stability data at ambient temperature for urea sensors obtained from multiple production batches made according to the invention in a three week use-life stability and 5-month shelf life stability studies.

Urea was measured daily in an aqueous sample with a high concentration of urea. (95 mg/dL) over the 3 week use-life on these cartridges to assess the sensor urea measurement linearity over time.

Figure 3A:
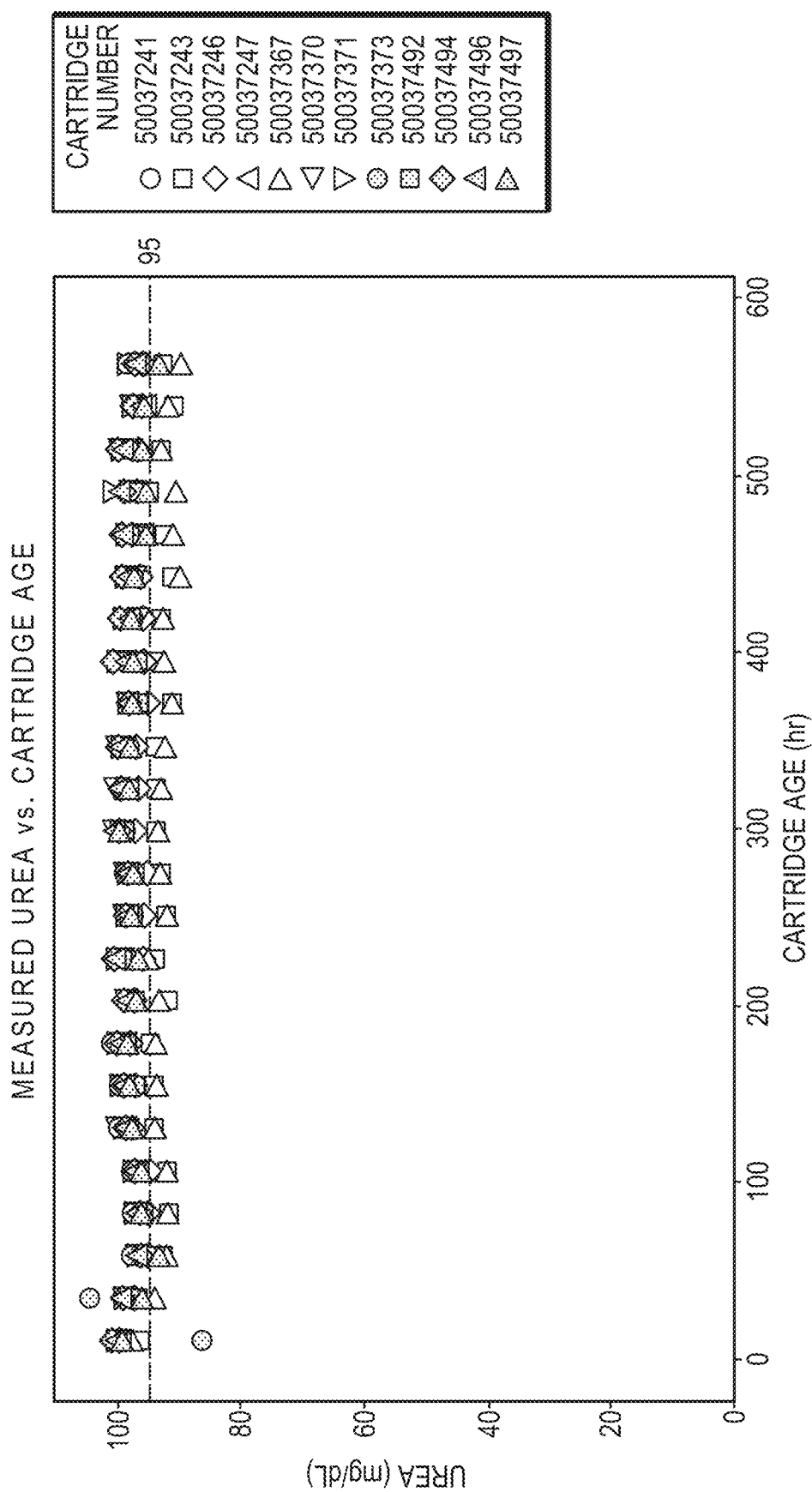
FIG. 3A is a graphic illustration of measured high urea concentration (95 mg/dL) versus cartridge age of twelve urea biosensors after short sensor shelf-life of two weeks and up to 3 week use-life; Daily urea concentration measurement in high urea sample (95 mg/dL) over 3-week use life.

FIG. 3A graphically illustrates urea measured in twelve urea sensors selected from three batches of sucrose treated sensors and short shelf-life storage at ambient temperature of two weeks. Daily measurement of the high urea concentration (95 mg/dL) sample over the three week use-life at short sensor shelf-life showed stable use-life performance with consistent measured urea concentration of about 95 mg/dl.

Figure 3B:
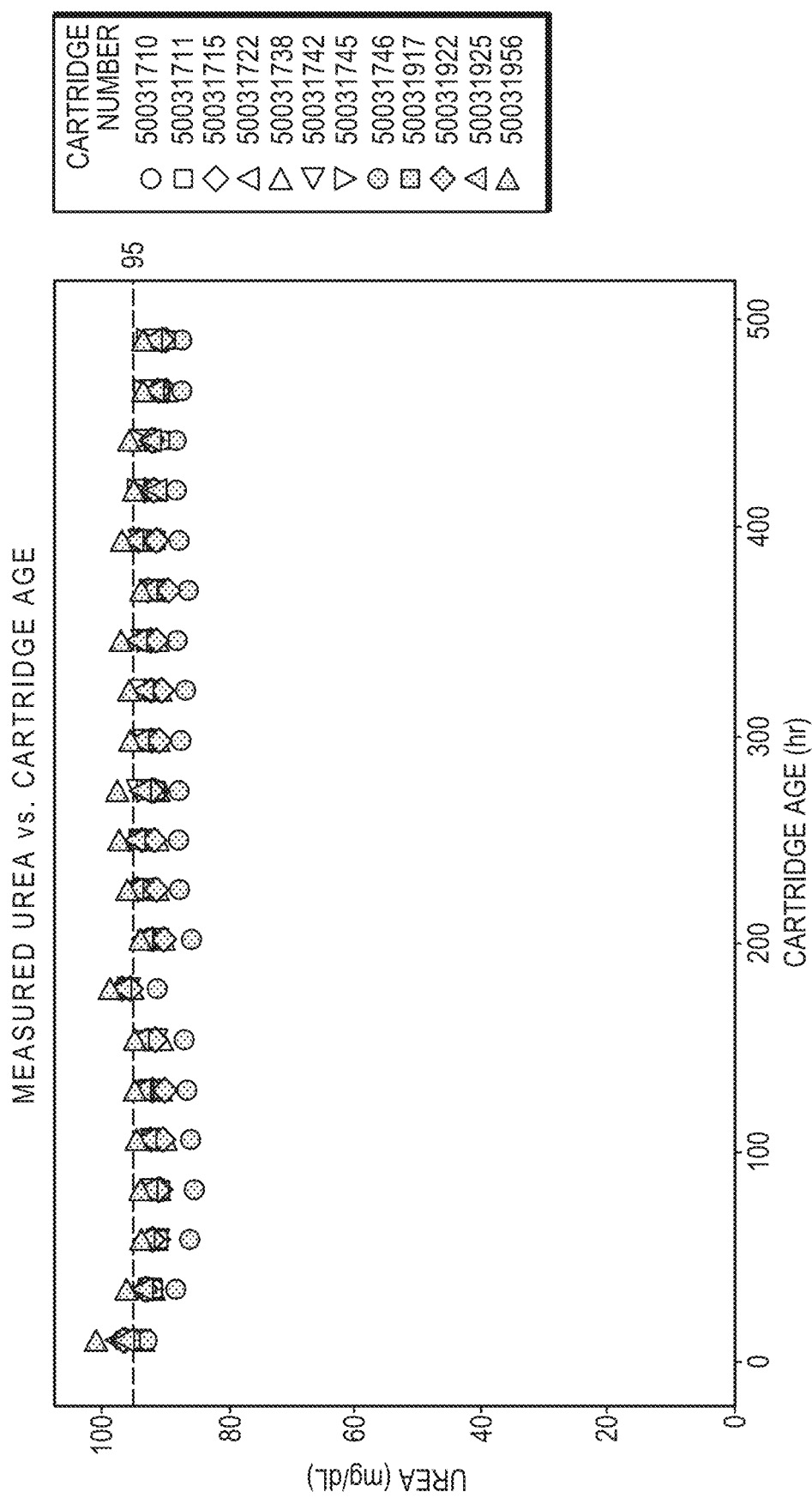
FIG. 3B is a graphic illustration of measured high urea concentration (95 mg/dL) versus cartridge age of twelve urea biosensors stored at ambient temperature over 5 months and up to 3 week use-life. Daily urea concentration measurement in high urea sample (95 mg/dL) over 3-week use life.

FIG. 3B graphically illustrates the results from another twelve urea sensors from three different batches of sucrose treated urea sensors. Daily measurement of the high urea concentration (95 mg/dL) sample over three-week use-life at 5-month ambient storage shelf life showed same stable use-life performance with consistent measured urea concentration of about 95 mg/dl.

By applying polysaccharide treatment, sucrose used as an exemplary polysaccharide in these studies, urea sensor activity and stability at ambient temperature storage shelf-life for 5 months was maintained.

The invention described above is applicable to urea biosensors developed on multiple urea sensor platforms.

We claim:

1. A urea biosensor comprising:
an ammonium-selective polymeric membrane;
an enzyme layer comprising urease on an outer surface of the ammonium-selective polymeric membrane;
a polymeric diffusion membrane on a surface of the enzyme layer to form part of a composite membrane; and
(i) polysaccharide that is over a combination of the polymeric diffusion membrane, the enzyme layer, and the ammonium-selective polymeric membrane or (ii) polysaccharide that is over a combination of the polymeric diffusion membrane, the enzyme layer, and the ammonium-selective polymeric membrane and that is added to the urease before the urease forms the enzyme layer on the ammonium-selective polymeric membrane, the polysaccharide for maintaining stable activity of the urease between the polymeric diffusion membrane and the ammonium-selective polymeric membrane.

2. The urea biosensor of claim 1, further comprising:
a metal element comprising silver, platinum, or gold; and
an inner electrolyte solution between the metal element and the ammonium-selective polymeric membrane.

3. The urea biosensor of claim 1, further comprising:
a metal element comprising silver/silver chloride; and
an inner electrode solution between the metal element and the ammonium-selective polymeric membrane.

4. The urea biosensor of claim 1, wherein the polymeric diffusion membrane comprises a polymer matrix and an ammonium-selective ionophore in the polymer matrix.

5. The urea biosensor of claim 4 wherein the polymer matrix comprises one or more of: polyvinyl chloride, polyurethane, poly(tetrafluoroethylene), poly(methyl methacrylate), silicone rubber, or a mixture of: polyvinyl chloride, polyurethane, polv(tetrafluoroethylene), poly(methyl methacrylate), or silicone rubber.

6. The urea biosensor of claim 4, wherein the polymer matrix comprises polyvinyl chloride.

7. The urea biosensor of claim 4, wherein the ammonium-selective ionophore comprises one or more of: nonactin, monactin, dinactin, trinactin, tetranactin, narasin, hexaoxaheptacyclotritrtracontane, benzocrown ethers, cyclic depsipeptides, or a mixture of: nonactin, monactin, dinactin, trinactin, tetranactin, narasin, hexaoxaheptacyclotritrtracontane, benzocrown ethers, or cyclic depsipeptides.

8. The urea biosensor of claim 4, wherein the ammonium-selective ionophore comprises nonactin.

9. The urea biosensor of claim 1, wherein the urease is cross-linked.

10. The urea biosensor of claim 1, wherein the polysaccharide comprises one or more of sucrose, trehalose, raffinose, or lactitol.

11. The urea biosensor of claim 1 wherein the polymeric diffusion membrane comprises a polymeric compound comprising polyurethane, poly(tetrafluoroethylene) ionomers, the perfluorosulfonate ionomer NATION®, poly-(2-hydroxymethyl methacrylate), polyvinyl chloride, cellulose acetate, or a mixture or copolymer of: polyurethane, poly(tetrafluoroethylene) ionomers, the perfluorosulfonate ionomer NAFION®, poly-(2-hydroxymethyl methacrylate), polyvinyl chloride, or cellulose acetate.

12. The urea biosensor of claim 1, the polysaccharide comprises 10% sucrose.

13. A disposable cartridge housing the urea biosensor of claim 1.

14. The disposable cartridge of claim 13, further comprising an array of sensors, the sensors comprising the urea biosensor.

15. A clinical analyzer for performing in vitro diagnostics, the clinical analyzer comprising the urea biosensor of claim 1.

16. A method for making a urea biosensor, comprising:
casting urease in solution on an outer surface of an ammonium ion-selective membrane of an electrode to form an enzyme layer;
applying a diffusion barrier on a surface of the enzyme layer;
after the diffusion barrier is applied to the enzyme layer, applying a polysaccharide solution to a structure comprising the diffusion barrier, the enzyme layer, and the ammonium ion-selective membrane of the electrode; and
drying the structure to form part of the urea biosensor.

17. The method of claim 16, wherein the urease is cross-linked.

18. The method of claim 16, wherein the urease is cross-linked by a chemical comprising one or more of: glutaraldehyde, 1,4-diisocyanatobutane, 1,2,7,8-diepoxyoctane, or 1,2,9,10-diepoxydecane.

19. The method of claim 16, wherein the electrode comprises silver, platinum, or gold.

20. The method of claim 16, wherein the electrode comprises silver/silver chloride electrode.

21. The method of claim 16, wherein the polysaccharide solution comprises sucrose, trehalose, raffinose, or lactitol.

22. The method of claim 16, wherein the diffusion barrier comprises one or more of: polyurethane, poly(tetrafluoroethylene) ionomers, the perfluorosulfonate ionomer NAFION®, poly-(2-hydroxymethyl methacrylate), polyvinyl chloride, cellulose acetate, or a mixture or a copolymer of: polyurethane, poly(tetrafluoroethylene) ionomers, the perfluorosulfonate ionomer NAFION®, poly-(2-hydroxymethyl methacrylate), polyvinyl chloride, or cellulose acetate.

23. The method of claim 16, wherein applying the polysaccharide solution comprises exposing the electrode to the polysaccharide solution for at least 30 minutes.

24. The method of claim 16, wherein the urea biosensor is configured to maintain stable urea measurement performance after 5 months of dry storage at ambient temperature and 21 days of use.

25. The method of claim 16, wherein a polysaccharide solution is added to the urease in solution before the urease in solution is cast.

26. The method of claim 16, wherein the polysaccharide solution comprises 10% sucrose.

27. A method for making a urea biosensor, comprising:
casting urease in solution on an outer surface of ammonium-selective polymeric membrane to form an enzyme layer;
applying a polymeric diffusion membrane to a surface of the enzyme layer to form part of a composite membrane;
(i) applying polysaccharide solution to at least part of a structure comprising the polymeric diffusion membrane, the enzyme layer, and the ammonium-selective polymeric membrane after the polymeric diffusion membrane is applied to the surface of the enzyme layer, or (ii) both applying polysaccharide solution to the at least part of the structure, after the polymeric diffusion membrane is applied to the surface of the enzyme layer and adding polysaccharide solution to the urease in solution before the urease in solution is cast on the outer surface of the ammonium-selective polymeric membrane; and
drying the structure, wherein the polysaccharide solution maintains stable activity of the urease between the polymeric diffusion membrane and the ammonium-selective polymeric membrane.

28. The method of claim 27, wherein the urease is cross-linked by a chemical comprising one or more of: glutaraldehyde, 1,4-diisocyanatobutane, 1,2,7,8-diepoxyoctane, or 1,2,9,10-diepoxydecane.

29. The method of claim 27, wherein the polymeric diffusion membrane comprises one or more of: polyvinyl chloride, polyurethane, poly(tetrafluoroethylene), poly(methyl methacrylate), silicone rubber, or a mixture of: polyvinyl chloride, polyurethane, poly(tetrafluoroethylene), poly(methyl methacrylate), or silicone rubber.

30. A urea biosensor comprising:
an ammonium-selective polymeric membrane;
an enzyme layer comprising urease on an outer surface of the ammonium-selective polymeric membrane:
a polymeric diffusion membrane applied to a surface of the enzyme layer to form part of a composite membrane; and
(i) polysaccharide that is applied to at least part of a structure comprising the polymeric diffusion membrane, the enzyme layer, and the ammonium-selective polymeric membrane after the polymeric diffusion membrane is applied to the surface of the enzyme layer, or (ii) polysaccharide that is added to the urease before the urease forms the enzyme layer on the ammonium-selective polymeric membrane, or (iii) polysaccharide that is both applied to the at least part of the structure after the polymeric diffusion membrane is applied to the surface of the enzyme layer and that is added to the urease before the urease forms the enzyme layer on the ammonium-selective polymeric membrane, the polysaccharide maintaining stable activity of the urease between the polymeric diffusion membrane and the ammonium-selective polymeric membrane;
wherein the urea biosensor is configured to maintain stable urea measurement performance after 5 months of dry storage at ambient temperature and 21 days of use.

* * * * *